(12) United States Patent
Hagedorn

(10) Patent No.: US 11,464,973 B2
(45) Date of Patent: *Oct. 11, 2022

(54) TRANSCRANIAL STIMULATION DEVICE AND METHOD BASED ON ELECTROPHYSIOLOGICAL TESTING

(71) Applicant: Evoke Neurosceince, Inc., New York, NY (US)

(72) Inventor: David W. Hagedorn, Jacksonville, NC (US)

(73) Assignee: Evoke Neuroscience, Inc, Jacksonville, NC (US)

(*) Notice: Subject to any disclaimer, the term of this patent is extended or adjusted under 35 U.S.C. 154(b) by 174 days.

This patent is subject to a terminal disclaimer.

(21) Appl. No.: 16/914,022

(22) Filed: Jun. 26, 2020

(65) Prior Publication Data

US 2020/0329968 A1 Oct. 22, 2020

Related U.S. Application Data

(63) Continuation of application No. 14/578,764, filed on Dec. 22, 2014, now Pat. No. 10,780,268, which is a continuation of application No. 14/531,012, filed on Nov. 3, 2014, now Pat. No. 8,958,882, which is a continuation-in-part of application No. 14/458,673, (Continued)

(51) Int. Cl.
| | | |
|---|---|---|
| *G06F 7/00* | (2006.01) |
| *A61N 1/36* | (2006.01) |
| *A61B 5/00* | (2006.01) |
| *A61N 2/00* | (2006.01) |
| *A61N 1/372* | (2006.01) |
| *A61N 2/02* | (2006.01) |
| *A61B 5/291* | (2021.01) |
| *A61B 5/375* | (2021.01) |

(Continued)

(52) U.S. Cl.
CPC ........ *A61N 1/36025* (2013.01); *A61B 5/0006* (2013.01); *A61B 5/291* (2021.01); *A61B 5/375* (2021.01); *A61B 5/377* (2021.01); *A61B 5/6803* (2013.01); *A61N 1/36014* (2013.01); *A61N 1/36031* (2017.08); *A61N 1/37247* (2013.01); *A61N 2/006* (2013.01); *A61N 2/02* (2013.01); *A61N 1/0484* (2013.01)

(58) Field of Classification Search
CPC ............ A61N 1/36025; A61N 1/36031; A61N 1/36014; A61N 1/37247; A61N 2/006; A61N 2/02; A61N 1/0484; A61B 5/291; A61B 5/375; A61B 5/377; A61B 5/0006; A61B 5/6803
USPC .................................................. 707/600–899
See application file for complete search history.

(56) References Cited

U.S. PATENT DOCUMENTS 8,088,058 B2 * 1/2012 Juliana .................. A61N 2/006
600/15

* cited by examiner

*Primary Examiner* — Isaac M Woo
(74) *Attorney, Agent, or Firm* — Woods Rogers Vandeventer Black; Timothy Bechen

(57) ABSTRACT

The present method and system provides for the clinical application of neurostimulation and/or neuromodulation to a patient. The method and system includes receipt and acquisition of patient data, processing of that data relative to one or more known data sets, and determination of a good-fit trigger specific treatment protocol. The method and system provides for application of the protocol to the patient, including delivery of neuromodulation and biofeedback. Based thereon, the method and system re-iterates the goodness of fit determination for further treatment to the patient.

20 Claims, 7 Drawing Sheets

Related U.S. Application Data filed on Aug. 13, 2014, now Pat. No. 8,938,301, which is a continuation-in-part of application No. 13/742,066, filed on Jan. 15, 2013, now Pat. No. 8,838,247, which is a continuation of application No. 13/543,204, filed on Jul. 6, 2012, now Pat. No. 8,380,316, which is a continuation of application No. 12/979,419, filed on Dec. 28, 2010, now Pat. No. 8,239,030.

(60) Provisional application No. 61/292,791, filed on Jan. 6, 2010.

(51) Int. Cl.
*A61B 5/377* (2021.01)
*A61N 1/04* (2006.01)

TRANSCRANIAL STIMULATION DEVICE AND METHOD BASED ON ELECTROPHYSIOLOGICAL TESTING

RELATED APPLICATIONS

The present invention is a continuation of claim and claims priority to U.S. patent application Ser. No. 14/578,764, filed on Dec. 22, 2014, which is a continuation of and claims priority to U.S. patent application Ser. No. 14/531,012, filed on Nov. 3, 2014, now issued U.S. Pat. No. 8,958,882, which is a continuation-in-part of and claims priority to U.S. patent application Ser. No. 14/458,673, filed on Aug. 13, 2014, now issued U.S. Pat. No. 8,938,301, which is a continuation-in-part of and claims priority to U.S. patent application Ser. No. 13/742,066 filed Jan. 15, 2013, now issued U.S. Pat. No. 8,838,247, which is a continuation of and claims priority to U.S. patent application Ser. No. 13/543,204 filed Jul. 6, 2012, now issued U.S. Pat. No. 8,380,316, which is a continuation of and claims priority to U.S. patent application Ser. No. 12/979,419 filed on Dec. 28, 2010, now issued U.S. Pat. No. 8,239,030, which is based on and claims priority to U.S. Provisional Patent Application Ser. No. 61/292,791, filed Jan. 6, 2010.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF INVENTION

The disclosed technology relates generally to the assessment and remediation of abnormal brain and physiological functioning, and more specifically to the utilization of transcranial stimulation within a clinical setting.

BACKGROUND

Traumatic brain injuries can result in physical and/or emotional dysfunction. Post traumatic stress disorder (PTSD) symptoms are similar to those of a mild traumatic brain injury (mTBI) and the two are difficult to differentiate using current assessment methodologies such as symptom assessments and questionnaires. In Army deployment, statistics have shown that upwards of 20% of soldiers suffer from mild traumatic brain injury (mTBI). Head and neck injuries, including severe brain trauma, have been reported in one quarter of United States service members who have been evacuated from Iraq and Afghanistan in the first decade of the 21st century A common cause of such injuries arises from exposure to percussive force from explosive devices. Further, recent military analysis indicates that over 90% of patients with acute mTBI will have vestibular (inner ear balance) disorders and those vestibular disorders are present in over 80% of persons with chronic mTBI symptoms. Likewise, stress disorders further affect numerous individuals, whether in a military or civilian situation. Brain injuries may further be incurred from car and bicycle accidents, sports accidents, falls, and the like. Up to 15% of persons suffering even a mild brain injury, or concussion, will suffer from persistent symptoms for more than a year, which significantly negatively affect their ability to work and function in daily life. It is estimated that there are currently 5.3 million Americans living with a disability as a result of a TBI. There are approximately 1.5 million diagnosed brain injuries in the U.S. annually, and it is estimated that another 2 million TBIs occur but are not properly diagnosed. Current assessment methods are either prohibitively expensive or do not diagnose the root cause of the suffering. Thus, there is a need in the art to accurately and quickly assess brain injury and associated dysfunction and then find ways to aid or enhance optimal functioning.

The brain is composed of about 100 billion neurons, more than 100 billion support cells and between 100 and 500 trillion neural connections. Each neuron, support cell and neural connection is extremely delicate, and the neural connections are tiny (approximately 1 micrometer). When the brain moves within the skull, such as occurs in rapid acceleration/deceleration (e.g., exposure to sudden impact and/or explosive devices), axons within the brain can pull, stretch and tear. If there is sufficient injury to the axon or support cells, the cell will die, either immediately or within a few days. Such damage can occur not only in the region that suffered direct trauma but in multiple regions (e.g., diffuse axonal injury). Loss of consciousness is not a prerequisite for mild traumatic brain injury and occurs in less than 5% of mild brain injuries, and head injuries such as diffuse axonal injury are not detectable in routine CT or MRI scan. High false negative findings may lead to patients being undiagnosed or misdiagnosed. Unfortunately current imaging methods still lack the resolution and sensitivity to determine functional brain capacity. Rating scales and other neuropsychological and functional examination methods have long been used to elucidate these functional questions, but they too are fraught with false negative results and limited specificity.

With the high prevalence of age-related cognitive decline conditions, injury from falls, cerebral-vascular events, neurodegenerative conditions (i.e., Alzheimer's Disease) and the many brain injuries occurring in sports and in military operation theaters, there is a need for a rapid and portable assessment instrument that can identify mTBI and neurocognitive dysfunction (e.g., balance, processing speed), direct and provide treatment interventions, track recovery progress, and aid in peak performance or the determination of return to leisure activities or duty.

BRIEF DESCRIPTION

An object of the disclosed technology is to utilize a brain-computer interface with electroencephalography and event-related potential (ERP) measures to localize brain injury and dysfunctional regions.

A further object of the disclosed technology is to provide low intensity direct current stimulation to dysfunctional brain regions as directed by the result(s) of electroencephalography (EEG) and event-related potential (ERP) measures.

Yet another object of the disclosed technology is to provide transcranial current stimulation (tCS) for selective stimulation, based on measures of brain activity and physiological characteristics and measures.

The disclosed method and system utilizes the described measurements and treatments in a clinical application using a multiple-phase processing technique. The multi-phase technique includes the multiple phases performed via one or more processing devices and accessing data sets stored in data sets. Based on measurement information acquired from and/or about a patient, and in comparison with standard data sets, the clinical methodology provides for iterative application of neuoromodulation to the patient.

The disclosed technology further includes user input and feedback functionality within a clinic or operational settings, whereby user measurements are collected, compared to one or more data sets and adjustments are made to the stimulation output. The data input can include measurement input, as well as clinician input recognizing various patient symptoms, as well as patient information such as medication information and general patient information. Based on the data collection, algorithms provide for adjustment of the stimulation, further measurements and further calculations of the changes to the patient from the adjustments. Therefore, the active utilization of the stimulation with additional data allows for application of the stimulation in a controlled environment for improving the efficacy of the stimulation.

In a method of the disclosed technology, electrophysiological data recording and analysis, with manual or automated delivery of transcranial current stimulation proceeds as follows. Via at least one electrode and at least one reference and ground electrode and, in one or more embodiments, a plurality of electrodes, non-invasive measurements of electrical currents produced by the brain of a person are conducted, including in one embodiment using a low intensity electromagnetic stimulation. This is done while directed stimuli, such as auditory or visual stimuli or balance tasks (for the purpose of examining brain reactions and processing of stimuli) are administered to the person being tested. A brain functional abnormality in the person, based on the conducting and the measuring, is determined. As a result of analysis of the brain electrical activity at rest and reactions and processing of stimuli, non-invasive brain stimulation takes place via said at least one anode electrode and said at least one cathode electrode to said brain of said person.

In embodiments of the above, a single electrode is surrounded by at least three electrodes. When the electrodes are used for stimulation purposes, the surrounding electrodes are of opposite polarity in a cluster. That is, an anode may be surrounded by three cathodes or a cathode may be surrounded three anodes. A plurality of such clusters may be utilized, such as by pre-placement in a helmet. Each cluster, or any single or plurality of electrodes, may be used to simultaneously or alternately stimulate different regions of the brain, based on the analysis described above.

The above-described analysis is augmented, in embodiments of the disclosed technology, based additionally on at least one additional measured/augmented physiological characteristic of a person. Such an additional measured/augmented physiological characteristic may be heart rate variability, a measure of balance, and measures of cognitive/ peak performance, and pathology comparisons.

The conducting of non-invasive measurement of electrical currents, as well as the non-invasive brain stimulation, may be carried out by way of a single device with a single manually-operated control. Or, the control may be pre-configured and automated. That is, electric current in the brain may be measured, an anomaly discovered, and a pre-programmed non-invasive stimulation is then carried out in the same portion of the brain as the anomaly, and, in embodiments, using the same electrode or electrodes to stimulate as were used to measure.

In a system of embodiments of the disclosed technology, a joint brain electro-analysis and transcranial current stimulation system is made up of a plurality of spaced-apart removable and replaceable electrodes arranged in a piece of headgear, an electroencephalography device wired to each of the electrodes, and a transcranial current stimulation device wired to each of the electrodes. In this system, upon measuring an electroencephalography anomaly in a brain region with the electroencephalography device, transcranial current stimulation is engaged to at least one anode and at least one cathode electrode of the brain region where the anomaly was measured.

An additional device may be used for measuring physiological characteristics of a person wearing the piece of headgear. Such an additional device may measure heart rate variability, balance, cognitive impairment, and/or make pathology comparisons.

The electroencephalography device and the transcranial current stimulation device may be contained within a single housing, may be operable with a single set of controls, or may consist of separate devices requiring manual disconnection of a wire hub to the electrodes, and connection to the other device.

In accordance with these and other objects, which will become apparent hereinafter, the disclosed technology will now be described with particular reference to the drawings.

Figure 1:
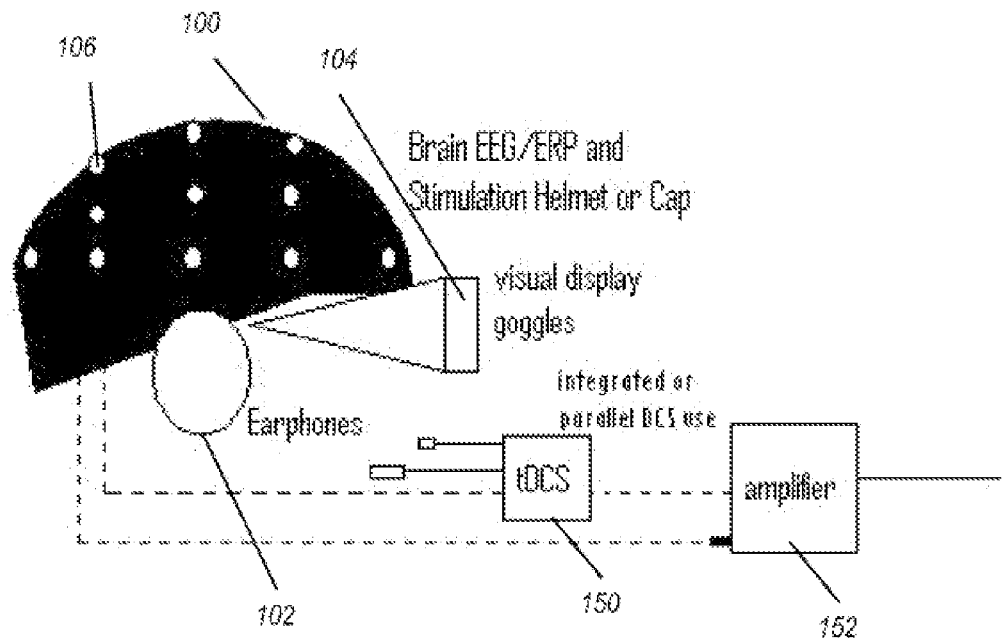
FIG. 1 shows a high level drawing of a device used to carry out embodiments of the disclosed technology.

A better understanding of the disclosed technology will be obtained from the following detailed description of the preferred embodiments taken in conjunction with the drawings and the attached claims.

DETAILED DESCRIPTION

Embodiments of the disclosed technology comprise systems and methods for assessing and repairing neurological pathways damaged by trauma or other brain-related dysfunction, as well as performing assessment and treatment operations in a clinical setting upon multiple users. The collection of data across multiple users may be used for testing or validation of a treatment technique. The methods comprise training a patient and stimulating brain areas where a functional abnormality (such as abnormal electrical activity outside a threshold of voltage, regularity, coherence, phase, and/or rate) has been detected. Such functional abnormalities are determined based on electroencephalography testing, a physiological test that passively monitors electrical current of at least one electrode positioned over the head of a test subject.

Systems of the disclosed technology comprise the use of an electroencephalogram (EEG) which functions by recording electrical activity from the scalp. The EEG measures electrical activity produced by the firing of neurons within the brain. In addition, an event-related potential (ERP) measurement may be used. An ERP, for purposes of this disclosure is a measured brain response that is time locked to a stimulus presented to the subject.

Physiological tests/measurements may be any one of, or a combination of, the following, and are, for purposes of this disclosure, defined as follows: Transcranial current stimulation (tCS)—application of non-invasive current stimulation via at least one electrode which is also usable or used for EEG measurements in embodiments of the disclosed technology. For purposes of this disclosure, non-invasive current stimulation also refers to cranial electrotherapy stimulation (CES), which is defined as small pulses of electric current along the head of a subject.

Transcranial magnetic stimulation (TMS) is electromagnetic induction to induce weak electric currents using a rapidly changing magnetic field to cause activity in specific or general parts of the brain, and used for measurement of cortical or distance measures of EEG and EMG for evoked response latency.

Low threshold transcranial magnetic stimulation (lt-TMS) is electromagnetic frequency emitted by way of one or more sensors placed against the scalp to produce a focal field to cause activity in specific or general parts of the brain, and used for neuronal modulation.

Electromyography (EMG) are measurements of electrical potential of muscles.

Computerized neurophysiological testing (NP) is used to estimate a person's peak level of cognitive performance. A person's raw score on a test is compared to a large general population normative sample and/or to the subjects own baseline measurement.

Force platform or balance plate—a stand-on device usable to determine balance and/or vestibular dysfunction. The balance plate can collect and/or record balance and/or postural data, such as the center of pressure and sway movement to analyze vestibular and balance function under different test conditions (e.g., unstable foam pad and eyes closed). The velocity of movement or excursion from balance position can be quantified for comparison to database norms. For some embodiments, the balance plate can be moved without the need for recalibration, for example its use in outdoor settings (e.g., sports, military arena). Collected data can be synchronized by software contained in one or more computers, with visual input stimuli, EEG, ERP and/or other parameters for time-locked variance measures associated with brain dysfunction. For some embodiments, the balance plate may be operated by way of an electrical current connection and instructions carried out by way of a computing device (see FIG. 8) or alternatively with a wireless connection between the plate and the computing device for portable use.

Repetitive transcranial magnetic stimulation (rTMS) includes generating a magnetic field that influences electrical activity in the brain. In rTMS, passing current through a coil of wire generates the magnetic field, the current provided in a repetitive fashion.

Psychological disorder screening—(such as for post-traumatic stress disorder), a component for vestibulo-ocular reflex dysfunction, a component for heart rate variability measures, a component for electroencephalography measures, and/or a component for transcranial magnetic stimulation (TMS) delivery with voltage isolator for simultaneous amplified cortical and distally evoked potential latency measures and motor threshold measures.

By way of the above measurements, while non-invasively monitoring EEG readings of one or multiple sites/regions of the brain, anomalies in neurological impulses are detected. The sites or regions of the brain are then stimulated. As little as one sensor may be used to stimulate, and this anode or cathode may be at the site where the anomaly was detected and may be via the same electrode used to locate the anomaly and which measured the anomalous EEG/ERP measurement. Such an electrode may be in a helmet worn by a user and allows for positive (to increase neural activity) or negative (to decrease neural activity) stimulation at the site where the anomaly was detected.

Such embodiments of the disclosed technology will become clearer in view of the following description of the figures.

FIG. 1 shows a high level drawing of a device used to carry out embodiments of the disclosed technology. A helmet 100 comprises at least one, or a plurality of, electrodes 106 (represented as white dots). The helmet may be any receptacle that holds the electrodes in a position relative to the head of a wearer, or alternatively, electrodes may be taped or otherwise placed on the head. Earphones 102, goggles 104 and/or another display device are used in embodiments of the disclosed technology to exhibit stimuli to a user, the stimuli used to vary measurable brain activity. The electrodes 106 are electrically connected to one of an electrical stimulation device 150 or electrical measuring device (e.g., a sensor), such as by way of amplifier 152. The same electrode or electrodes may be disconnected from one such device and connected to another such device, such as by way of changing an electrical pathway (switch) or by physically disconnecting an electrical wire from one device, and plugging into another. In embodiments of the disclosed technology, the electrical stimulation and measuring devices are housed within the same physical device and comprise a switch for changing the electrical pathway, which is manually operated or controlled by pre-programmed instructions. In other embodiments, the measuring device and stimulation device are in separate housings or devices, and only one is electrically connected to the electrode or electrodes 106 at one time. In other embodiments, the electrical stimulation and measuring devices are housed within the same physical devise but have separate outlets to which the electrode(s) may be unplugged and attached. Other devices, not shown, include force platforms (measure postural deviations of person), devices to alter the display on the goggles 104, and devices to alter the sound through the earphones 102, and input devices such as a computer mouse, keyboards, and joysticks.

Referring now to visual stimuli exhibited on a display device, such as the goggles 104 of FIG. 1, the visual stimuli produced may be an "immersive environment," for example a virtual reality 2- or 3-dimension moving "room" displayed through a virtual reality headset. The data collected from the balance plate, heart rate monitor, EEG, and so forth, can be used in conjunction with the visual stimuli for neurophysiological trauma assessment and/or rehabilitation training. The data collected from this component, as well as all other components may be linked with data collected from other components (e.g., EEG, ERP) for assessment purposes.

The system shown in FIG. 1 may further comprise a vestibular activation test (VAT) headset permitting a computerized test that monitors the vestibulo-ocular reflex (VOR) during natural motion. A VAT headset useful for the systems described herein may produce images and/or record eye movements. Images displayed in the VAT headset may be generated by computer-implemented instructions and transmitted via electrical impulses to the VAT headset via wireless or direct connection. Eye movements may be recorded by way of the VAT headset. The VOR is a reflex eye movement that stabilizes images on the retina during head movement by producing an eye movement in the direction opposite to head movement, thus preserving the image on the center of the visual field. As ocular trauma is often concomitant with traumatic brain injury, this component allows additional assessment of injury.

In a clinical or controlled environment, the stimulation techniques described herein are enhanced based on the inclusion of additional data sources and measurements. As described in further detail below, algorithmic processing of multiple data points generate good-fit determinations that trigger individual treatment protocols. Those protocols help define stimulation parameters, such as type of stimulation, location, amount, duration, etc. Moreover, data collection techniques described herein allow for data collection, further processing of the efficacy of the treatment protocol and further adjustments as necessary.

Figure 2:
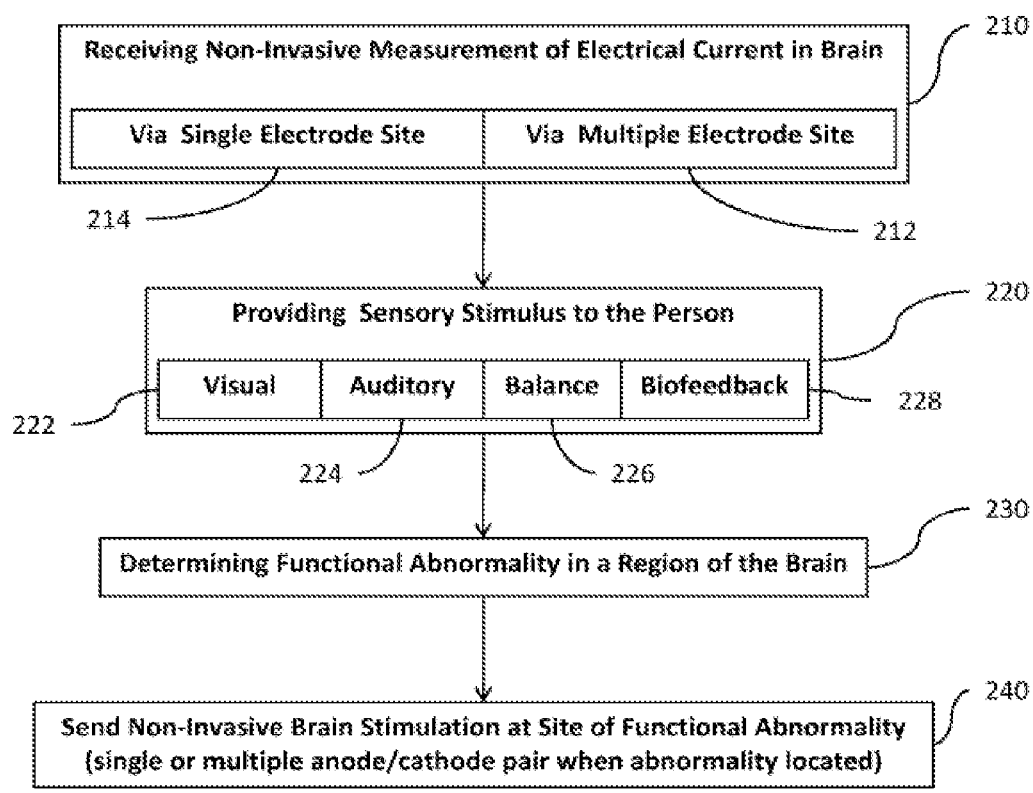
FIG. 2 shows a high level block diagram of a method of carrying out embodiments of the disclosed technology.

FIG. 2 shows a high level block diagram of a method of carrying out embodiments of the disclosed technology. In step 210, non-invasive measurements are made of electrical current in the brain of a test subject. This is accomplished by way of electrodes placed on a test subject, such as in a helmet shown in FIG. 1. In this manner, EEG and ERP signals may be recorded, measured, and analyzed. A single electrode may be used to carry out the measuring in step 214, or a plurality of electrode pairs may be used in step 212. The position of the electrodes is known, and each electrode or a grouping thereof is placed over a definable region of the brain, the region defined by a person carrying out embodiments of the disclosed technology. The region is defined as a specific brain area of interest for the recording, as defined by a person carrying out embodiments of the disclosed technology and may be a region covered by a single electrode pair or as large as half a hemisphere of a brain. Electrodes may also be grouped into clusters, such as with a single anode surrounded by three or more cathodes, or a single cathode surrounded by three or more anodes. Such clusters are electrically connected, such that electric current flows non-invasively through the proximal tissue from anode(s) to cathode(s), stimulating the brain (stimulating, herein is defined as passage of electrical current through the brain and includes increasing or decreasing neuron activity at a site).

While conducting step 210, typically, step 220 is also carried out which comprises providing sensory stimulus to a person. This may be done by way of, for example, the goggles shown in FIG. 1 for a visual stimulation 222, auditory stimulation 224, balance stimulation 226, biofeedback measurements 228, or other sensory stimulations known in the art. Definitions and examples of various types of such stimulations are provided above, before the description of the figures.

Stress tests and peak performance tests may also be performed to determine, for example, how many times a minute a person is able to respond to a stimulus, or how long a person can hold his/her breath or balance on a force platform, etc.

Based on the electrical measurements, that is, EEG or ERP measurements, an abnormality in a region of the brain is determined in step 230. An abnormality may be any of the following: electrical activity which is too infrequent, too frequent, too low in amplitude, too large in amplitude, an improper pattern of electrical activity, inter-intra-hemispheric connectivity, electrical activity in the wrong portion of the brain for the stimulus given, or the like.

In step 240, based on the located functional abnormality, non-invasive brain stimulation (such as tCS) is administered at the region of the abnormality. In certain cases, the same electrode which was used to measure the electrical impulses within the brain is used to administer tCS or other electrical stimulation. This tCS may be low intensity electromagnetic stimulation, such as rTMS technology or lt-TMS technology. In this manner, accuracy of the stimulated region may be assured, as there is no difference in the physical location on the head where the existing electrical impulse was measured, versus where the new electrical stimulation is administered. The place of administering may be as little as a single anode/cathode pair (or cluster), or may use multiple anode/cathode pairs (or clusters).

Figure 3:
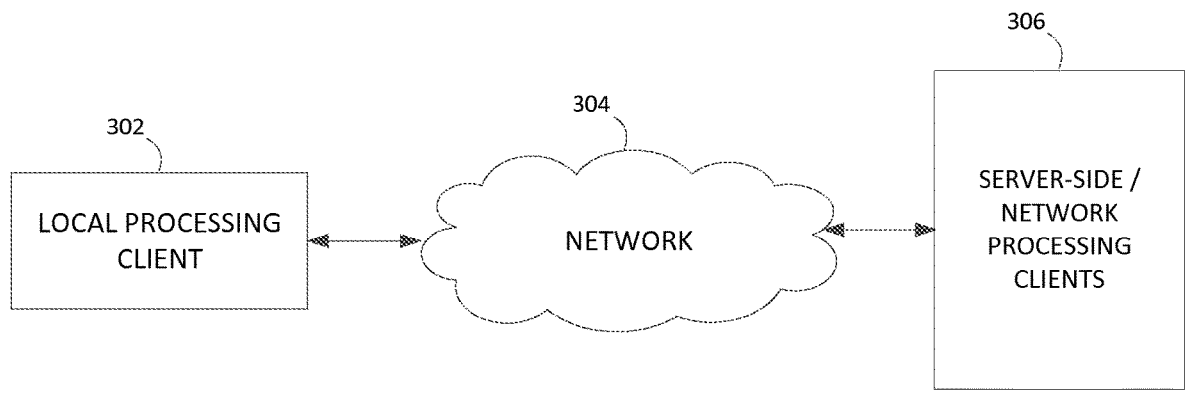
FIG. 3 shows an exemplary processing environment including a cloud or network-based processing client.

Whereby the device of FIG. 1 provides for collection of data, FIG. 3 illustrates an embodiment of processing environment providing for the remote database and data analysis method and system operations. In this system, the local processing client 302 may be any suitable local processing device including but not limited to the collection of measurement data, and/or one or more processing systems for executing interface operations. For example, in one embodiment the local processing client may be a personal computer or a tablet computer having a browser or application for executing the interface functionality described herein.

The network 304 may be any suitable network providing communication thereacross. In one embodiment, the network 302 is an Internet connection across a public access network, wherein it is recognized that the network may include a private and/or secure network, as well as network exchanges via one or more service providers. The network 304 operates to facilitate the communication of data between the local processing client 302 and the server-side network processing clients 306.

The server-side network processing clients 306 may be any suitable number of network-processing devices. In one embodiment, the client 306 may be a dedicated processing server, wherein in another embodiment, the client 306 may be any suitable number of distributed computer resources for processing operations as described herein.

Tests are used to measure psychological characteristics of a test subject. The purpose of at least some of these tests is to assess the ability of the test subject to automatically and fluently perform relatively easy or over-learned cognitive tasks relevant to the ability to process information automatically or rapidly and measure executive function complex decision-making capacity. Test can be performed on one or more suitable devices, such as a processing device providing a display. Such tests include, but are not limited to, trails making test, grooved pegboard, symbol-digit test, digit coding, symbol search, Stroop test, finger-tapping tests, categories test, Wonderlic tests and Wechsler subtests, Wisconsin Card Sort Test, matrix reasoning, Raven Progressive Matrices tests, and/or components of the neuropsychological assessment batteries. Still another type of test is a test of malingering (e.g., TOMM) which can be part of a comprehensive assessment of both mTBI (mild traumatic brain injury) and PTSD, as such tests aid in determining actual impairment resulting from neurophysiologic impairment as opposed to subject feigning or exaggerating. Such tests can assist in minimizing false positive mTBI diagnoses. Psychological questionnaires, for example a set of questions designed to diagnose a particular psychological disorder, such as PTSD, can also be included in computerized or hard copy form.

An additional component, a single pulse (0.9-1.5 tesla) fixed or variable Hz setting transcranial magnetic stimulation (TMS) device may be linked to a voltage isolator with linked amplifier for synchronized EEG, ERP and/or electromyogram (EMG) recordings or low threshold magnetic stimulation (lt-TMS) that operates independent of a voltage isolator. The amplifier (such as amplifier 152 of FIG. 1) may be a multichannel amplifier for multiple modality physiological measurements (e.g., EMG, ERP, EEG, temperature, blood volume pulse, respiration, skin conductance, EKG, blood pressure, etc.). Sensors for each physiological measurement may also be connected to the amplifier, for example as a means to collect measurements from a test subject. TMS is a non-invasive technique utilizing magnetic fields to create electric currents in discrete brain regions. Typically, during TMS, a time-pulsed magnetic field is focused on cortical tissue via a coil placed near the area to be affected (e.g., M 1, Dorsolateral Prefrontal Cortex (DLPFC)). TMS can be utilized for various measurements of intracortical inhibition and facilitation, for example short interval intracortical inhibition (SICI), long interval intracortical inhibition (LICI) and contralateral cortical silent period (CSP). Such measurements can aid in differential diagnosis between individuals with mTBI and mTBI with PTSD. Any commercially available TMS device known in the art may be utilized. For some embodiments, the TMS device utilized is portable.

Low intensity electromagnetic stimulation has been shown to have certain and safe clinical value, with rTMS technology being one example. Low threshold stimulation below that of rTMS available in this device is called low threshold transcranial magnetic stimulation (lt-TMS). This electromagnetic stimulation is one of the methods utilized in this device yet with the added benefit of being able to apply such stimulation to one or more location points on the scalp within a given session or predesigned treatment sequence to stimulate along a neuronal network rather than one location along that network.

The lt-TMS is delivered using either a pulsed (or pulse-train) or sinusoidal electromagnetic stimulation waveform and is delivered based on the manual operation of the device or programed delivery based on deviation measures from a normative or comparison database of collected EEG and ERPs produced by the same device. The device is designed to record electrophysiology allowing for a pre and post measure of such electrophysiology when utilizing any of the stimulation types within the device (tDCS, tACS, tRNS, lt-TMS).

While rTMS has limitations of stimulation rate below 20-30 Hz due to heat, the selection of lt-TMS within the device allows for longer session durations and faster stimulation.

In one embodiment, lt-TMS delivery can be performed manually at either one or multiple locations. Delivery at multiple locations can be done simultaneously or in timed preselected or preprogrammed sequence of locations. Another benefit of lt-TMS is the real time measuring of the electrophysiology before and after stimulation. The electrophysiology can also be measured as part of a preprogrammed stimulation sequence. Furthermore, lt-TMS electromagnetic stimulation permits longer stimulation durations without heating the neuronal tissue and with a larger range of frequency selections 0.1-100,000 Hz.

Figure 4:
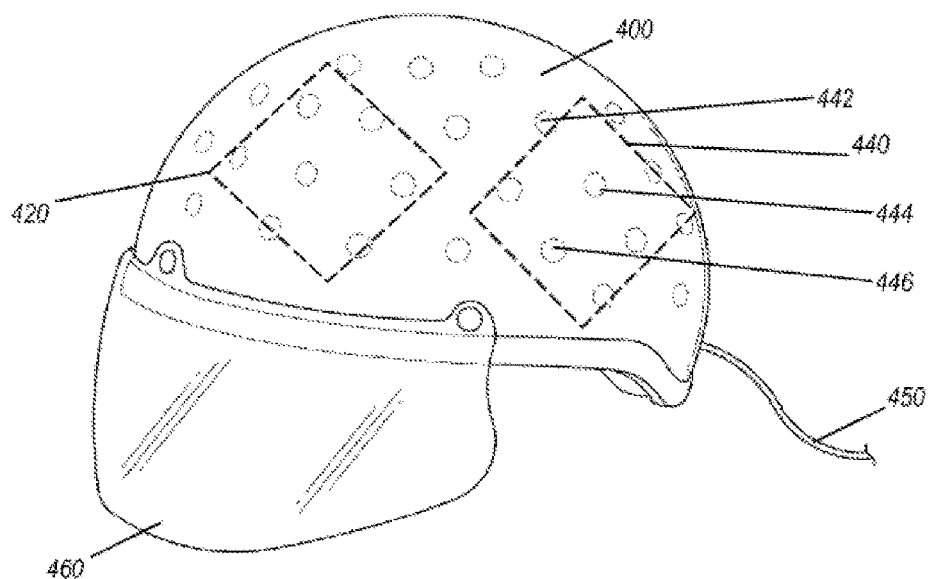
FIG. 4 shows a perspective view of a helmet with electrodes used in embodiments of the disclosed technology.
Figure 5:
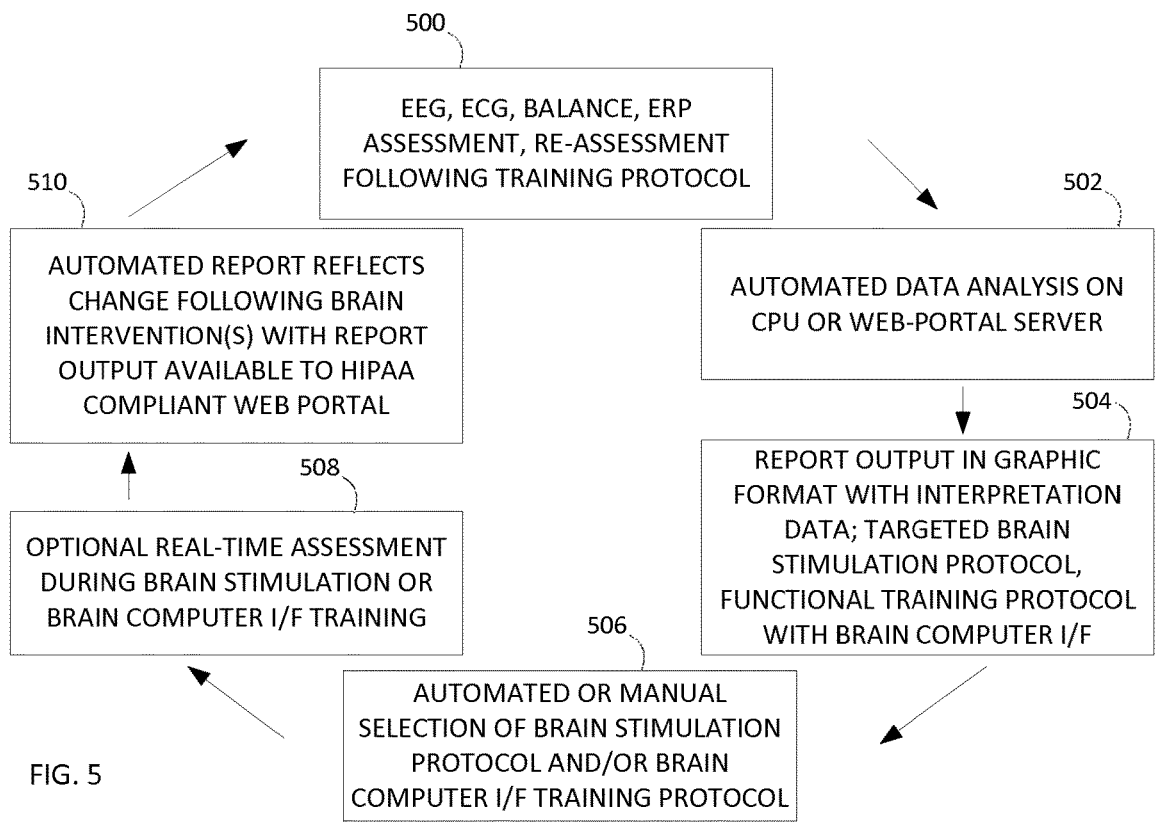
FIG. 5 illustrates one embodiment of a flow diagram for data analysis.

FIG. 4 shows a perspective view of a helmet with electrodes used in embodiments of the disclosed technology. FIG. 5 shows a bottom view of such a helmet. The helmet 400 comprises multiple electrodes, such as electrodes 442, 444, and 446. As can be seen in the figure, a plurality of electrodes are spaced apart around the interior of a helmet or other piece of headgear and are adapted for both reading electrical activity from the brain of the wearer and delivering new impulses. That is, by way of a single electrode, plurality thereof, cluster of electrodes, or plurality of clusters, a joint brain electro-analysis and transcranial current stimulation system (tCS) comprises a plurality of spaced-apart removable and replaceable electrodes arranged in an item of headgear. An electroencephalography device (such as an EEG) is wired to each of the electrodes, as is a transcranial current stimulation device (at the same time or alternating by way of a switch or plugging/unplugging a cable between the devices). In one embodiment, using lt-TMS, the stimulation sensors are smaller than conventionally larger (25-35 cm2) in order to provide both a quality electrophysiology measure and to deliver a more focal stimulation.

Due to the know dielectric properties of skull and scalp tissue the device permits a dose-response adjustment such that the user can adjust frequency and intensity according to measured electrophysiology changes taken at the stimulation location or all scalp locations (e.g., EEG amplitude, EEG coherence, ERP amplitude and latency) and accordingly adjust stimulation thresholds to a level of desired neuronal tissue modulation.

A cable 450, which will be discussed at greater length with reference to FIG. 6, allows for electrical connectivity between the electrodes and either or both of a tCS and EEG device. Further, a viser 460 is integrated with the helmet in embodiments of the disclosed technology for optical stimulation (e.g. a video monitor). The device cap/helmet is constructed with an optional extension cable and materials such that simultaneous magnetic resonance imaging can occur while the device is in use.

Upon measuring an electroencephalography anomaly in a brain region with the electroencephalography device, transcranial current stimulation is engaged to at least one anode and at least one cathode electrode to the brain region where said anomaly was measured. Additional devices, as disclosed above, such as a force plate, visual stimuli utilizing interactive games and tests, and the like, may also be utilized. The transcranial current stimulation device, in embodiments of the disclosed technology, is engaged only when either a) data from the electroencephalography device indicates that electrical impulses in the brain are outside a predefined range/threshold of where they should be or where is desired by the administrator of the device; and/or b) when the additional physiological characteristic, as measured with another device disclosed in the specification herein (such as an EMG device, balance plate, pathological test, etc.) is out of range of a predefined allowable threshold. Thus, the ability to administer tDCS may be limited by the above factors and, as a safety measure, may be further limited automatically by way of pre-programmed instructions in a computer device (see FIG. 8) or manually by way of a physician or other clinical practitioner relying on such data.

The device delivers subthreshold polarization that potentially causes polarization at the soma and thereby obtains deeper brain source penetration and delivers a greater effect with a least intrusive and in a safer manner than high intensity stimulation. The device permits a programming of stimulation type (tDCS, tACS, tRNS, lt-TMS) delivery interrupted by electrophysiology measures (e.g., EEG, ERPs) in order to ascertain the relative difference each stimulation type has on neuronal activation or suppression such that the most efficient and effective intervention can be then applied for the individual.

Referring further to a force plate (which includes a "balance plate" in embodiments of the disclosed technology), the device is used as follows. The force plate collects (and may record) balance and/or postural data, such as center of pressure, sway movement, and movement velocity to analyze vestibular and balance function under different test conditions (e.g., unstable foam pad and eyes closed). For some embodiments, the balance plate may be moved without the need for recalibration, for example use in outdoor settings (e.g., sports, military arena). Collected data may be synchronized with visual input stimuli, EEG, ERP and/or other parameters for time locked variance measures associate with brain dysfunction. In some instances, visual stimuli are provided to a subject while the subject utilizes the force plate. The visual stimuli produced may be an "immersive environment", for example a virtual reality 2- or 3-dimension moving "room" displayed through a virtual reality headset. The data collected from the force plate is used, in embodiments of the disclosed technology, for neurophysiological trauma assessment and/or rehabilitation training.

As further seen in FIG. 4, the anodes and cathodes may be in a cluster 420 and 440. The clusters shown are by way of example. That is, one anode (e.g., 444) may be surrounded by three or more cathodes (e.g., 442, 446, and others), or one cathode may be surrounded by three or more anodes. Anodes and cathodes have opposite polarity, and where neural activity is too high in a region, a cathode may be used to suppress activity. Where neural activity is too low in a region, an anode may be used to increase activity. This may be done between two electrodes, a cluster, or a plurality of clusters. In two different regions, it may be desired, in embodiments of the disclosed technology, to stimulate (or de-stimulate) simultaneously. In this context, "simultaneously" may be defined as being at the same time or alternating. Different rates of stimulation at each region may also be used, as necessary. That is, two regions that should not be linked, in fact are. By firing at different times or rates, in different regions (at the second region, firing from 0 to 180 degrees off, in a phase between two firings of the first electrode), two synced regions may be brought out of phase. This may normalize brain activity as regions of the brain require specific phase similarities and differences depending upon their relative function. Similarly, by firing at the same time, two out of sync regions may be brought in phase. Now, the two regions are said to have coherence. Biofeedback (a user viewing his/her own EKG, EEG, ERP, or other indicators of physiology function) may be utilized in conjunction with the tDCS, so as to give the user the ability to consciously control his or her brain or other physiological activity to help the healing process when attempting to normalize brain or physiological function (e.g., heart rate variability) activity.

The electrodes may be separable, so as to be individually placed, or may be within a sized EEG cap or helmet (such as helmet 100 of FIG. 1). The electrodes, which can also be used as anodes and cathodes for purposes of tDCS, may be directly connected to one or more stimulation devices (e.g., tDCS or CES stimulation) and/or measuring devices (e.g., EEG recording device) simultaneously, or via a switch or removable plug to switch between such devices. When measuring EEG/ERP readings (electrical impulses from the brain of a user), various activities (stimuli or physiological measurements) may take place simultaneously. A finger depression device may be used, and others such as a force platform, heart rate monitor, EMG (muscle electric potential), interactive biofeedback devices allowing the user to monitor internal activity (directly or by way of a game used to control by way of biofeedback), and the like. These measurements may then be compared against a database of known human population normative values as indications to determine a deviation from normal function, check the deviation against what is being monitored by way of EEG measures and abnormalities of electric impulses in the brain, and in some embodiments, a correlation may be made to determine brain abnormalities associated with different dysfunctions. In other embodiments, the brain abnormalities will serve to verify a particular dysfunction. In still further embodiments, based on prior determined data of brain electrical abnormalities for a specific pathology, tDCS or other electrical stimuli (e.g., CES) is then induced at a region where the brain abnormality is measured.

For example, a database may contain reference EEG components for normal and known pathological results (e.g., IED blast brain trauma, motor vehicle accident brain trauma, Attention Deficit Disorder, Alzheimer's disease). In some instances a database may comprise subcategorization of data from collected EEG and ERP data. Comparison of subject EEG and ERP results to such databases can allow for EEG and ERP analysis as part of the diagnostic process. Source localization methods (to determine specific regions of interest and dysfunction) may be accessed for selected EEG and ERP components.

When transcranial current stimulation (tCS) is used as a result of the above measures, the current may be via the EEG electrodes or can be delivered by other anode and cathode electrodes (i.e., anode sensors or cathode sensors placed from a different system) designated for tCS treatment. For example, sponges may be attached to graphite composite sensor pads sized for anode and/or cathode to ensure proper contact with the subject. The tCS device, in embodiments of the disclosed technology, directs anodal or cathodal non-invasive brain stimulation to one or more of the connected site locations on the subject. Stimulation can be delivered as transcranial current, or other effective current type, in amounts between about 0.25 mA and 6.0 mA.

Upon measuring an electroencephalography anomaly in a brain region with the electroencephalography device, transcranial direct current stimulation is engaged to at least one anode and at least one cathode electrode to the brain region where said anomaly was measured. Additional devices such as a force plate, visual stimuli utilizing interactive games and tests, and the like, may also be utilized.

As used herein, the tCS may be transcranial direct current stimulation (tDCS) or transcranial alternating current stimulation (tACS). The data collection techniques and operations, as described in U.S. Pat. Nos. 8,239,030; 8,380,316; and 8,838,247 are herein incorporated by reference.

The data is collected and thus provided to one or more remote data processing systems. These remote data processing systems may be connected via a networked connection, including in one embodiment an Internet-based connection. In additional embodiments, the networking may be via a private or secure network. Wherein, it is noted that Internet-based connections include the processing of security features with the data, to insure the privacy of the data during transmission.

For example, one embodiment may include a data collection computing device, such as a personal computer or other type of processing device, operative to receive the electrophysiology data. The processing device therein provides for the encryption or inclusion of security features on the data and the transmission to one or more designated locations. For example, one embodiment may include the compression of the data into a ".zip" file.

The server further provides for the storage of the data and retention of data information. In this embodiment, the server creates a postscript formatted file, such as a PDF file and the database is then updated to include storage of this information. In one embodiment the database further includes enhancements to maximize storage, including determining if the data to be stored is duplicative. If the data is duplicative, a single data link can be provided, but if the data is not duplicative, then separate access to the data is provided.

The data acquired from the device may be processed locally or across network. In a typical embodiment, the user or client is a doctor or other medical specialist having the ability to review, understand and advise a patient based on the data generated in the reports. As noted above, the data generated in the reports relate to the electrophysiology data acquired from patients.

The complete system consists of a wireless amplifier equipped to record artifact free electrical signals from the brain and heart and also position in space using a nine or greater accelerometer. This same device is configured to deliver electric current back to the sensors that are in contact with the scalp in order to facilitated non-invasive brain stimulation. Sensors make contact with this skin using either dry sensors or electro dermal gel or saline impregnated sensor for consistent sensor to skin connectivity measured by impedance.

The software provides for automated data collection using script software and self-guided instructions. The software sends the resulting data for algorithm processing either on the CPU or on a dedicated secure server through an internet connection. This data is processed on the CPU and processed either on the installed database and processing software or transmitted to the cloud-based server where processing takes place.

The data analysis is returned in a report format showing physiology graphics and interpretive results from which the user can make intervention or diagnostic decisions. Several comparison databases can be selected from within the software to provide a comparison measure for the data analysis. Pre-set EEG training protocols (e.g., theta:beta ratio training for attention; alpha:theta ratio training for relaxation) are configured for automated home or clinic based training.

Individual baseline data can also be utilized so that the individual's data can be compared to an earlier data sample. An example of this is a professional athlete having his or her pre-season baseline that is used for comparison following a concussion. This is particularly useful for single-subject design research of change over time and intervention results. Group databases such as peak performance or pathology comparison databases (i.e., Alzheimer's disease sample database) are also available for selection and data comparison. Intervention options include real-time noise and artifact removal algorithms that permit EEG and ECG training devoid of movement and other disruptive artifact or signal noise. Individual differences from the selected comparison database permits specific or individually derived interventions as non-invasive brain stimulation (e.g., tDCS/tACS) and brain computer interface (sLORETA/eLORETA brain computer interface, wavelet time-frequency neurofeedback, event-related potential neurofeedback; Brodman Area selection, neurofeedback, neuro-network brain computer interface) and peripheral biofeedback such as heart rate variability biofeedback).

The brain computer interface or neurofeedback can include any number of operations or techniques, including for example low resolution brain electromagnetic topography source localization feedback and surface electroencephalography amplitude or phase or coherence feedback.

The user receives report and intervention information from cloud-based server interface or from optional embedded software on the CPU for usage where internet connectivity is not possible.

The results of the data analysis include a protocol that directs the non-invasive brain stimulation sensor placements and current parameters. These stimulation protocols can be manually or automatically selected to provide the user with both brain compute interface training and brain stimulation or brain modulation interventions.

The rapid assessment and re-assessment of the brain and other measures included in the physiology measurement battery allows for rapid determination of brain computer interface training location and frequency protocols and also brain stimulation or modulation using electric current. The re-assessment quantifies the difference from the baseline measure in order to generate a report showing the change made by either or both brain computer interface and electric current brain modulation.

The re-assessment then provides an updated intervention protocol. Protocols will vary based on the assessment results such that the different locations on the scalp may be stimulated with different polarity at the sensor and with more or less milliamps than one another. Users can manually define scalp location, polarity at the sensor, and milliamp levels and duration at each location. Users can also select from pre-defined protocols to increase or decrease regional neuronal activity.

The same data analysis report provides illustration and instruction on the current flow through the brain tissue in order to further quantify the cortical excitability relevant to the users clinical or performance intent. Current flow reporting aid the user with further and more specific brain modulation targeting protocols using Talairach locations and Brodmann Areas. The availability of the data analysis and reports on the web portal allows for telemedicine access and review.

The sensors permit real time stimulation with electrical current and simultaneous recording of EEG using signal filters that remove the electrical stimulation and permit only the EEG and event related potentials to be recorded and processed. This feature permits the user to combine targeted brain stimulation with brain computer interface training using real time artifact correction. Simultaneous neurofeedback with stimulation allows for data analysis showing the focal changes or modulation in the brain from the individual or combined intervention modalities.

FIG. 5 illustrates a circular data flow diagram representing the circular operations described herein. Step 500 includes the assessment and re-assessment protocols, such as EEG, ECG, Balance, ERP, etc. Step 502 is the automated data analysis on a CPU or networked server. Step 504 is the report output, which may include output in graphical format with interpretation data. The report 504 may further include targeted brain stimulation protocol, functional training protocol with brain computer interface.

Continuing in the cycle of FIG. 5, step 506 is the automated or manual selection of brain stimulation protocol and/or brain computer interface training protocol. Step 508 is an optional real-time assessment during brain stimulation or brain computer interface training. Step 510 provides automated reporting that reflects changes following brain intervention(s) with report output, which can be available to a user including HIPAA-compliant web or network portals.

Figure 6:
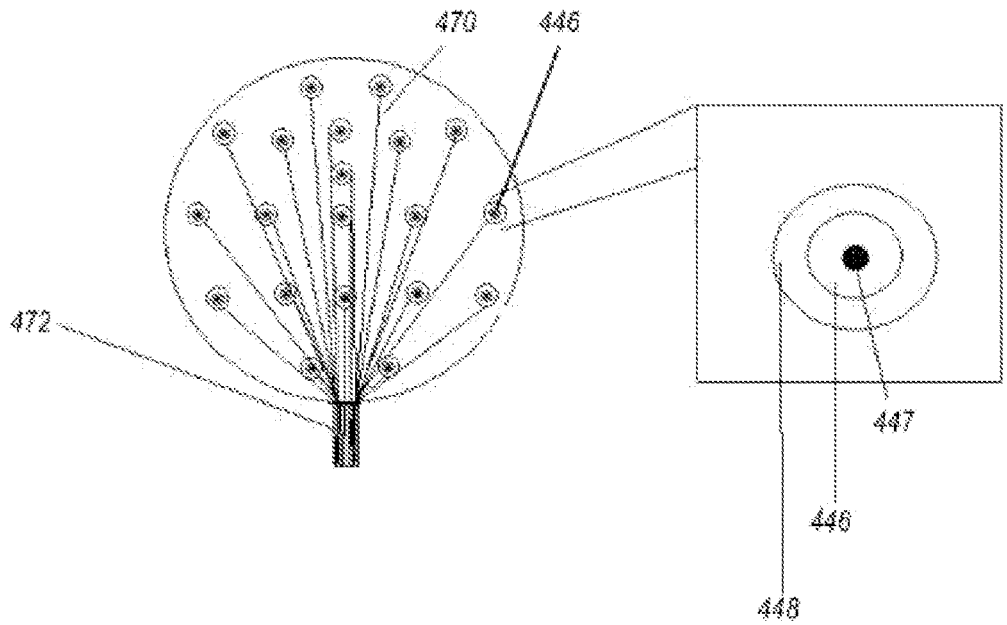
FIG. 6 shows electrical pathways to electrodes within a helmet of an embodiment of the disclosed technology.

FIG. 6 shows electrical pathways to electrodes within a helmet of an embodiment of the disclosed technology. Electrical connections (such as connection 470) provide an electrical pathway to and from each electrode and join at a cable 472 housing all electrical connectors between each electrode and an amplifier or other equipment for sending and/or receiving electrical impulses. Each electrode, such as electrode 446 comprises the electrode itself (typically, a metal or other known conductor, the conductor being removable from an electrode housing 448 with disposable electrode boot 449 in embodiments of the disclosed technology) with a hole 447 for inserting conductive gel.

Figure 7:
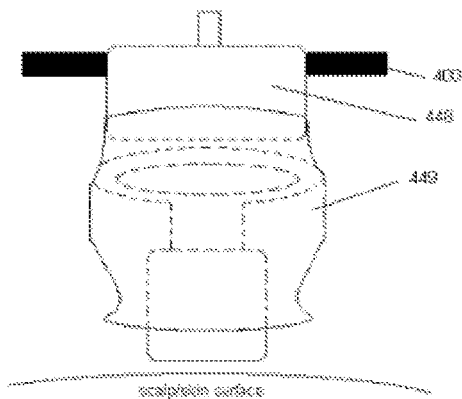
FIG. 7 is a side view of an electrode with disposable electrode boot attachment used in an embodiment of the disclosed technology.

FIG. 7 is a side view of an electrode with disposable electrode boot used in an embodiment of the disclosed technology. An encasement 448, such as one made of hard plastic covers the electrode. The electrode 449 is attached within the helmet 400. A disposable foam conductive patch is inserted, in embodiments of the disclosed technology, into an electrode sensor. Conductive gel permits a conductive connection from the electrode, and by extension the foam patch insert, to the skin. This connection permits both the recording of cortical electrical activity and the delivery of anodal or cathodal direct current. Two version of this electrode are available: (1) the first version is a soft rubber boot that can be wrapped around a hard plastic electrocap device. This soft boot slips onto any of the electrocap sensors and has within it a porous foam or sponge pad. The connective gel that is inserted into the electrocap hole also flows into this boot as shown in the art. (2) A second version is a harder plastic, carbon, or graphite material replacement sensor that connects to any wire harness for EEG/ERP and may be built into a helmet or softer cap.

In an embodiment of the disclosed technology, a single interface is used to control EEG, ERP, and tCS and is electrically or wirelessly connected/engaged with any one of or a plurality of inputs including ECG sensors, a balance plate, a headset, a tCS cap, or the like. Between the input devices and the interface may be a voltage isolator and/or amplifier. The interface, or a separate computational device may be used for data collection and analysis from the EEG/ERP cap and other inputs. Visual images may be displayed on a headset and visual and auditory stimuli may be provided by way of a monitor and speakers, respectively.

Figure 8:
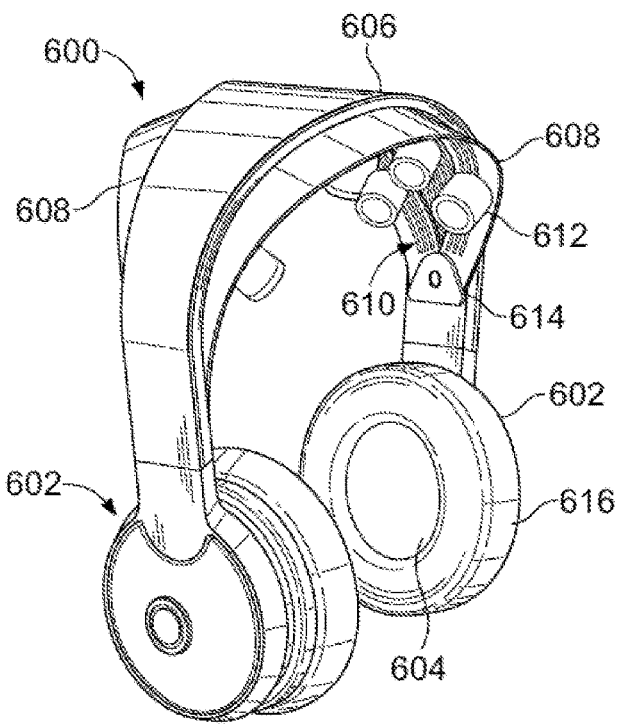
FIG. 8 illustrates another embodiment of a headgear.

FIG. 8 illustrates another embodiment of a device for collecting data and providing user feedback. This device 600 includes earpieces 602 with speakers 604. The device 600 further includes a top cross-bar 606 and side-bars 608, the bars, 606 and 608, having a track 610 thereacross with sensors 612 disposed therein. The device 600 additionally includes a hinge 614 for the side-bars 608. Further embodiments include an articulating arm 618 having a lens 620 thereon.

The headgear 600 may be composed of one or more suitable materials, including plastic, metal or carbon fiber by way of example. The earpieces 602 are representative embodiments of engagement portions providing for engaging the user's head and securing placement of the sensors 612. In the illustrated embodiment of FIG. 6, the speakers 604 are disposed within the engagement portions of the earpieces 602, providing for the audio output of sound consistent with known speaker technology. In this embodiment, the earpiece 602 and speaker 604 include cushioning 616 that not only improves user comfort in wearing the device, but also improves sound isolation of the speaker to minimize or reduce any ambient noise.

The cross bar 606 and side bars 608 include the track 610 that allows for the insertion of the sensors 612. The sensors 612 may be any suitable sensors that connect into the track for electrical connection with the device 600. In one embodiment, the sensors 612 are dry sensors, where the dry sensors are attached using magnets for easy removal and replacement in-between users and for alternate sensor or electrode type attachments. The same system both provides EEG/ERP measures but also delivers brain stimulation using direct current and/or alternating current, as described above.

When worn by a user, the sensors 612 are in contact with the user's cranium, wherein the location of the sensors 612 can be adjusted by movement of the sensor 612 along the track 610 within the cross-bars 606 and 608.

The hinge 612, disposed on both sides of the cross-bar 606, allows for the articulation of the of the side bars 608 away from or towards the cross-bar 608. Therefore, when worn by the user, the sensor 612 location of the user's cranium can also be adjusted by the inward or outward articulation of the side bars 608.

In embodiments including the arm 618 and the lens 620, the headgear 600 allows for the visual display of content on a lens, not expressly shown. The positions or location of the lens relative the user can be adjusted by the adjustment of the arm 618. The arm 618 includes wiring (not readily visible) for providing an output signal to the lens. In one embodiment, the lens may be a high-definition lens operative to provide a visual output viewable by the user, where as described herein, the user can be subjected to visual stimuli for feedback generation via the headgear. In this embodiment, the lens operates similar to the visual display goggles 104 of FIG. 1 or the visor 460 of FIG. 4.

The above data collection and stimulation operations provide for clinical operations for improving and optimizing neurostimulation functionality. As used herein, a clinical operation is not expressly limited to a clinic, such a medical or rehabilitation clinic, but can additionally include an location wherein the use of the operations described herein are performed.

Moreover, the described methodology is functionally operational based on one or more processing devices operating in conjunction with one or more databases as well as a neurostimluation device as described herein.

Figure 9:
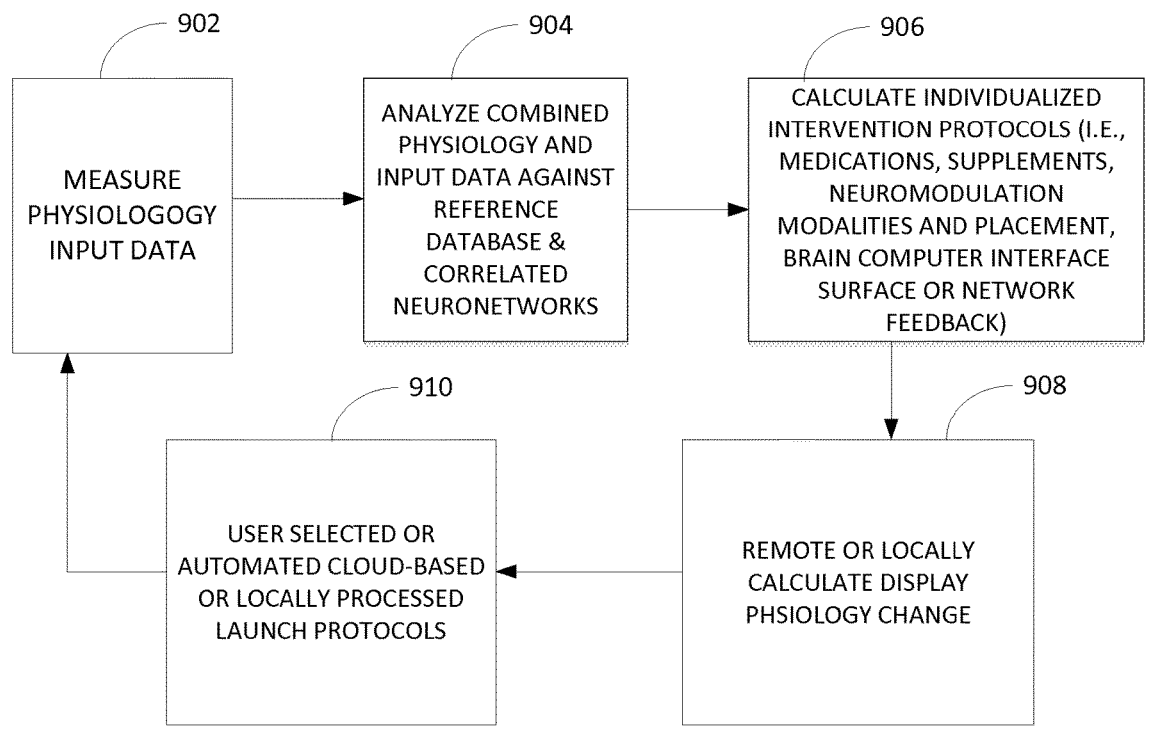
FIG. 9 illustrates a data flow diagram illustrating an overview of one embodiment of a clinical application process.

FIG. 9 illustrates a generalized flowchart of one embodiment of the clinical application for neurostimulation. The methodology is quantified into five categories, a data collection phase, a data analysis phase, an intervention selection phase, an invention delivery phase, and a change analysis. The phases noted in FIG. 9 are described in greater detail in FIGS. 11-15 below.

The methodology of the phases are performed using processing devices for computations, accessing databases for the acquisition of various data sets, measuring and testing devices for the acquisition of patient information, as well as computing interface(s) for data collection, e.g.

patient questionnaire, as well as the utilization of the herein described neuromodulation device for application of stimulation to the patient.

Phase 902 is the receipt of input of the measured physiology data. Phase 904 is the analysis of combined physiology and input data against reference database and correlated neuronetworks. Phase 906 is the calculation of individualized intervention protocols. Such protocols may include, but are not expressly limited to, medications, supplements, neuromodulation modalities and placement, brain computer interface surface network or network feedback. Phase 908 is the display of physiology change, calculated either locally or remotely. Phase 910 is the user selection or automated network-based or locally processed launch protocols. In one embodiment, the methodology is iterative, wherein step 902 is therein repeated.

Figure 10:
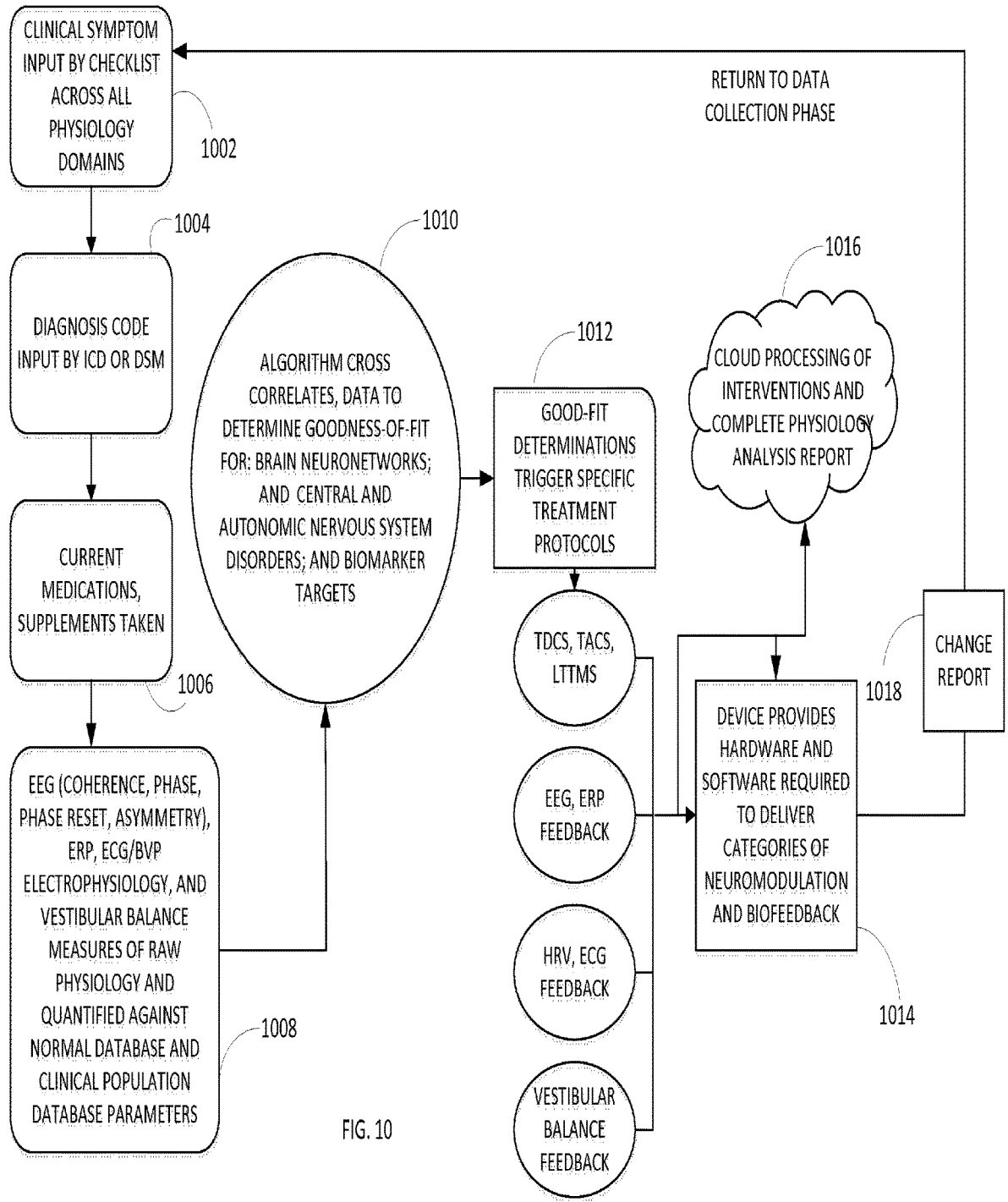
FIG. 10 illustrates a phase-based flow diagram of one embodiment of a clinical application process.

FIG. 10 illustrates another flow diagram of multiple embodiments of the clinical use application described herein. While iterative in nature, the first illustrated step, step 1002 is the receipt of clinical symptoms based on checklists across physiology domains. Step 1004 is receipt of diagnosis code by ICD or DSM. Step 1006 is receipt of current medications and any supplements taken by a patient. Step 1008 include receipt of measurement data, such as but not limited to EEG, ERP, ECG/BVP Electrophysiology, and Vestibular Balance measures of raw physiology and quantified data against normal database and clinical population database parameters.

In step 1010, the methodology provides for cross correlation of data to determine good of fit for: brain neuronetworks; and central and autonomic nervous system disorders; and biomarker targets. This step may be performed based on one or more processing devices accessing one or more databases having data sets therein.

Step 1012 provides that good-fit determinations trigger specific treatment protocols, such as the exemplary list of protocols for neuromodulation and biofeedback in FIG. 10.

Step 1014 includes one or more processing devices providing hardware and software required to deliver the neuromodulation and biofeedback from the various protocols. In another embodiment, or in addition to step 1014, step 1016 provides for cloud-based or network-based processing of interventions and complete physiology analysis report.

Step 1016, provides for a change report. This report indicates adjustments to the neuromodulation and biofeedback. Thereupon, the clinical operations revert back to a data collection phase of collection data about the patient to further iterate the treatments using neuromodulation and biofeedback.

Figure 11:
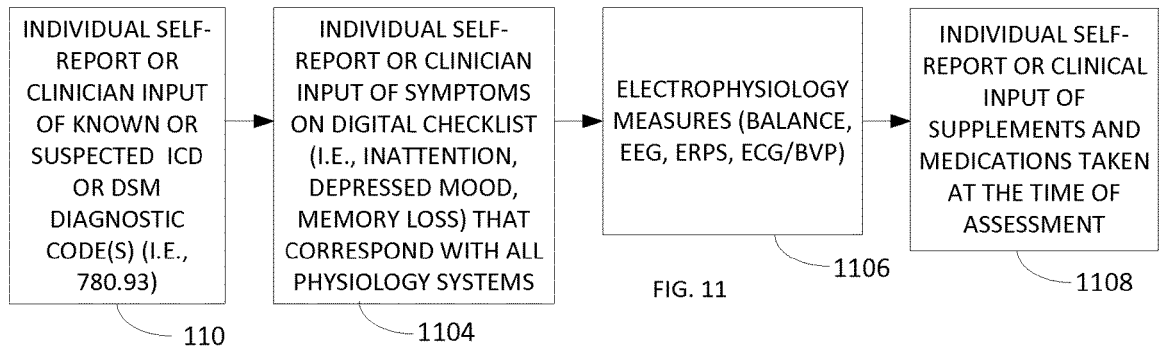
FIG. 11 illustrates a data flow diagram of one embodiment of a measured physiology plus input data phase of the clinical application process.

FIG. 11 illustrates one embodiment of the acquisition of data relating to the patient, including measured physiology and other input data. Step 1102 is the receipt of individual self-reporting or clinician-input of known or suspected information. One embodiment may include the inclusion of ICD or DSM diagnostic codes. This data may be received via any suitable data processing interface, including via data entry a user interface, accessing a patient database, or any other suitable means.

Step 1104 is the receipt of the input of symptoms. One embodiment may include selection or recognition on a digital checklist. Symptoms, by way of example, may include lack of attention to detail, depressed mood, memory loss, among others. The input of step 1104 may include input to any or all physiology systems of the patient.

Step 1106 is the receipt of electrophysiology measures. Exemplary measures include balance, EEG, ERP, ECG/BVP. Wherein receipt of these measures may be acquired, in one embodiment, using the techniques described above, including techniques relating to FIGS. 1-7.

Step 1108 is the receipt of individual or self-reporting or clinical input of supplements or medications taken at the time of assessment. Similar to step 1104, this input may be via any suitable interface including data entry or in another embodiment accessing a related database having the data therein.

The input of data may include additional data, wherein the steps 1102-1108 are exemplary and not limiting in nature. Thereupon, in one embodiment, the first phase (phase 902 of FIG. 9) is completed based on the collection of data described herein.

Figure 12:
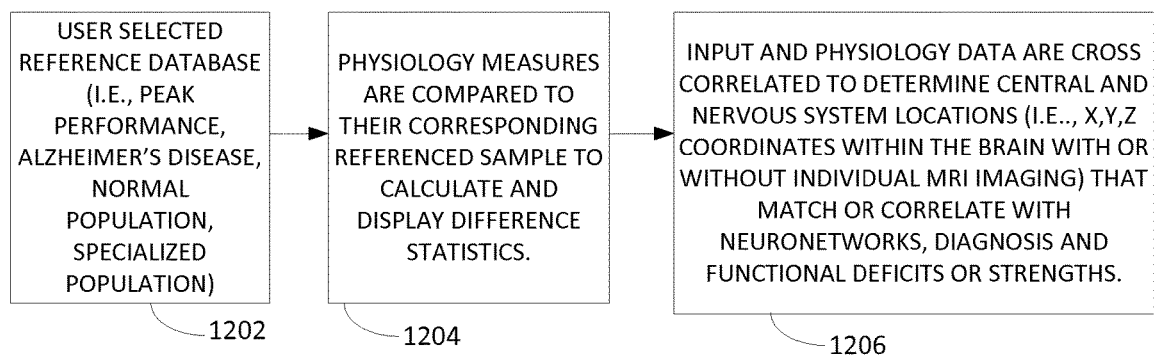
FIG. 12 illustrates a data flow diagram of one embodiment of an analysis-combined physiology and input data phase of the clinical application process.

FIG. 12 illustrates steps relating the second phase, phase 904 of FIG. 9. This phase relates to the analysis of data based on reference data. Not expressly illustrated herein, the methodology includes access to one or more databases having the referenced data therein. The reference database(s) may be locally or remotely stored, wherein access may be using recognized database accessing protocol(s).

Step 1202 is accessing the user selected reference database. This database may be selected in reference to an underlying or anticipated condition of the patient. The database may be selected based on requested reference data for further processing of the input data. For example, the reference database may include peak performance data, Alzheimer's data, normal population data, specialized population data, etc.

Step 1204 provides for comparing physiology measure to corresponding referenced sample data as may be acquired in step 1202. The comparing in step 1204 provides for calculating and displaying differences in the data sets, in one embodiment.

Whereupon, in step 1206, input and physiology data are cross correlated to determine central and nervous system locations (i.e. x, y, and z coordinates within the brain with or without individual MRI imaging) that match or correlate with neuronetworks, diagnosis and functional deficits or strengths. Thereupon, in one embodiment, step 1206 generates generalized location information for the application of neurostimulation based on the data calculations described herein.

Scalp electrical potentials are recorded from the surface placed electrode sensors and solutions (eLORETA, sLORETA) to the inverse problem are used to source intracranial signals for using more than one method of localization. One example of this method to compute cortical current density with optimized localization capacity and dynamic functional connectivity in the brain is by the use of eLORETA published by Roberto D. Pascual-Marqui. Reference: Pascual-Marqui. R D, Lehmann, D, Koukkou, K, et al. (2011). Assessing interactions in the brain with exact low-resolution electromagnetic tomography. *Philosophical Transactions of the Royal Society A,* 369, 3768-3784.

Figure 13:
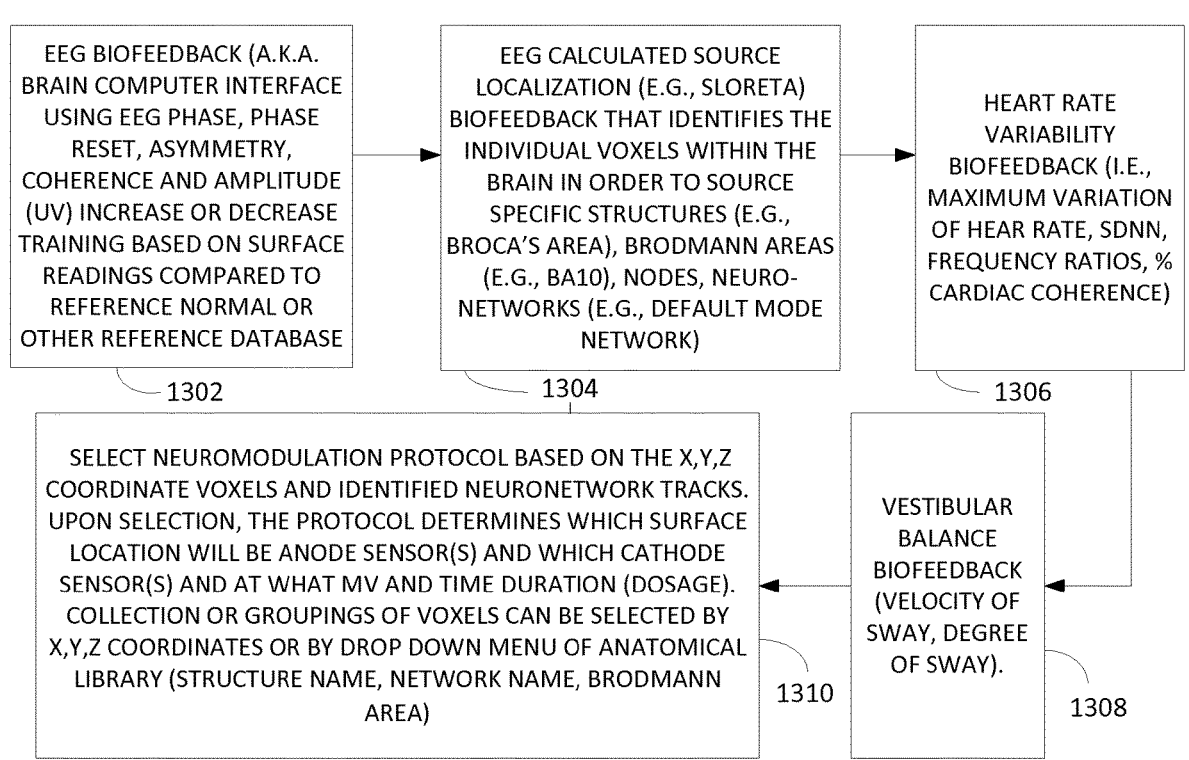
FIG. 13 illustrates a data flow diagram of one embodiment of calculating individualized intervention protocols phase of the clinical application process.

FIG. 13 illustrates steps relating to the calculation of individualized intervention protocols, Phase 906 of FIG. 9. Step 1302 is the EEG biofeedback, such as a brain computer interface using EEG Phase, Phase Reset, Asymmetry, Coherence and Amplitude (uV) increase or decrease training based on surface readings compared to reference normal or other reference database data.

Step 1304 is the EEG calculation source localization, e.g. sLORETA, biofeedback that identifies the individual voxels within the brain in order to source the specific structures, Brodmann areas, nodes, and/or neuro-networks.

Step 1306 is the determination of heart variability biofeedback, i.e. maximum variation of heart rate, SDNN frequency ratios, percentage cardiac coherence. This step may be performed by reading heart rate variability biofeedback information from the data acquisition described above.

Step 1308 is the determination of vestibular balance biofeedback, such as by way of example velocity of sway and degree of sway. Similar to step 1306, this data can be acquired based on the data acquisition techniques described above.

Step 1310 is the selection of neuromodulation protocols based on the x, y and z coordinate voxels and the identified neuronetwork tracks.

Upon selection, the protocol determines which surface location with be anode sensors(s) and which cathode sensor(s) and at what MV and time duration (e.g. dosage). In one embodiment, the collections or groupings of voxels can be selected by x, y, z coordinates or by drop down menu using an anatomical library (e.g. structure name, network name, Brodmann Area).

Measurements and quantification of the physiology (e.g., EEG, ECG, ERPs, balance) are obtained using sensor array and other electronic measurement components (i.e., gyroscope, accelerometer) and processed with algorithms for signal cleaning, artifact removal, and interpretive analysis against norm groups. Additional subjective data collected is computed for goodness-of-fit, such as noted below, to ensure ample overlap of objective and subjective data so that physiology findings is consistent with symptom complaints or peak performance objectives. Voxels, or clusters or neurons, are targeted using source localization x, y, z mathematics (i.e., sLORETA) and each voxel or mega-voxel (larger cluster of voxels) are calculated for normalcy against normal or special population databases for several functional measures to include 1 Hz bins frequency amplitude, coherence, phase, phase reset. Those voxels that fall outside of set normal limits or targeted peak performance limits (e.g., z-score+/−1.0) are listed for intervention targeting with combined or in isolation neuromodulation techniques to include pulsed or non-pulsed ultrasound neuromodulation, tDCS, tACS, magnetic field and brain computer interface, balance training, heart rate variability biofeedback, or other user defined and delivered interventions. Follow the intervention process a repeat assessment is calculated based on the differences across all physiology measures and differences across subject/patient self-report data submitted. The cycle can repeat until pre-selected normal or peak performance limits are achieved or the user choses to disconnect the cycle of measurement, modulate, train, re-measure.

Figure 14:
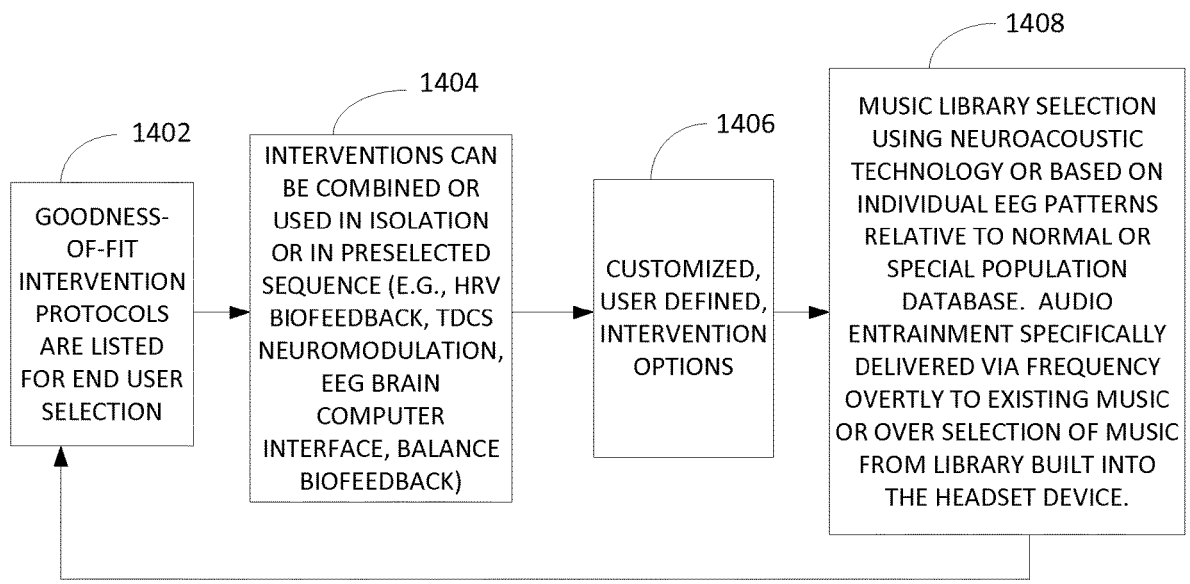
FIG. 14 illustrates a data flow diagram of one embodiment of a user selection or automated launch protocols phase of the clinical application process.

FIG. 14 illustrates steps of one embodiment of the user selected or automated launch protocols, phase 908 of FIG. 9. Step 1402 provides that goodness-of-fit intervention protocols are listed for end user selection.

Goodness-of-fit refers to overlapping physiology biomarkers (e.g., low 8-12 Hz EEB power in locations F3 relative to location F4; Brodmann Area 25 z-score greater than—1.5) known to correlated with subjective selection of symptoms or signs (e.g., lethargy, flat affect, insomnia) and additionally current diagnostic labels (e.g., Major Depression). A correlational analysis of the available data both confirms the relationship between symptoms and biomarkers but also calculates a quantified degree of severity from a normal health sample group.

Step 1404 provides that interventions can be combined or used in isolation or in a preselected sequence. For example, a heart rate variability biofeedback, tDCS neuromodulation, EEG brain computer interface, balance biofeedback.

Step 1406 provides for any customized user defined intervention options. Step 1408 is the selection of a music library using neuroacoustic technology or based on individual EEG patterns relative to normal or special population database data. In one embodiment, audio entertainment may be specifically delivered via frequency overtly to existing music or over selection of music from a library built into a headset device, such as the device of FIG. 8.

In one embodiment, the methodology of FIG. 14 therein reverts back to step 1402 for further modulation, adjustment, refinement or processing, if necessary.

Figure 15:
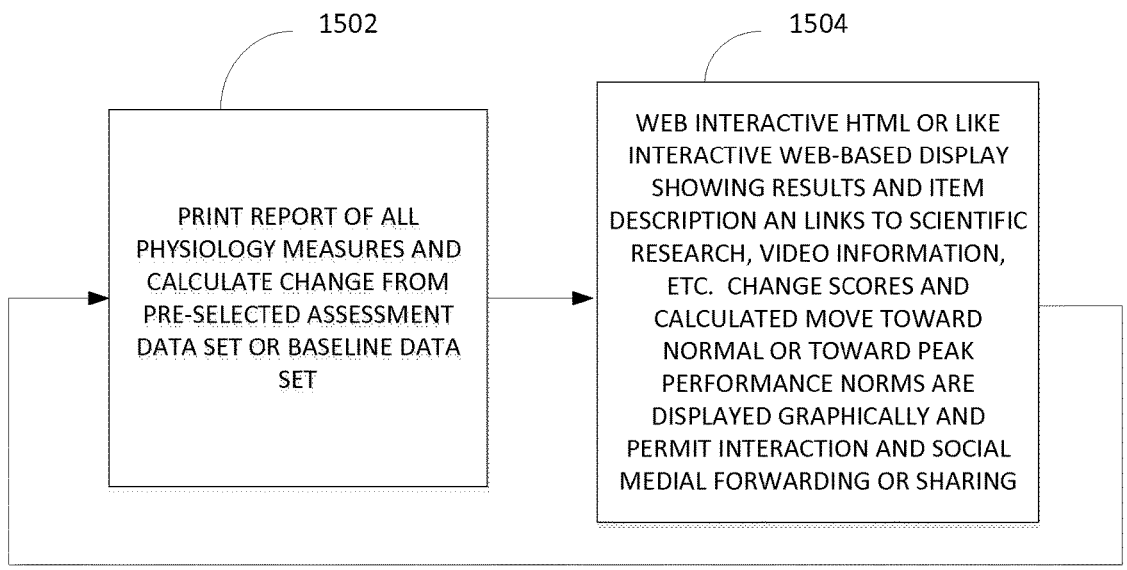
FIG. 15 illustrates a data flow diagram of the phase for calculating and displaying physiology changes of the clinical application process.

FIG. 15 illustrates steps of the phase for calculation and display of physiology change, phase 910 of FIG. 9. Step 1502 is the printed report of all physiology measures and calculated change from pre-selected assessment data set or baseline data set. In one embodiment, the report provides the deltas or changes in values over any number of selected intervals. For example, one embodiment can be changes over a full treatment period. In another example, the changes can be from a previous or prior treatment iteration. Moreover, the printed report may be modified or adjusted to customize for specific features or changes, as recognized by one skilled in the art.

Step 1504 is the generation of web interactive HTML or similar network-based interactive display showing results and item descriptions. The interactive display may include active links to associated content, such as scientific research, video data, etc. The display may additionally include graphical information plotting measured changes across time periods.

Therein, via the utilization of processing devices, databases having data sets stored therein and equipment described herein, the present clinical application allows for iterative treatments to the patients. The iterative treatments operate within a feedback loop to further enhance the effectiveness of the treatment for the patient.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the disclosed technology.

What is claimed is:

1. A transcranial stimulation method comprising:
   determining a treatment protocol for a patient based at least on a plurality of good-fit determinations; and
   applying a transcranial current stimulation based on the treatment protocol to the patient via:
   a plurality of spaced-apart removable and replaceable at least one of: electrodes and sensors, arranged in a piece of headgear;
   an electroencephalography device wired to one or more of said at least one of: electrodes and sensors; and
   a transcranial current stimulation device wired to one or more of said electrodes based on the treatment protocol.

2. The method of claim 1 further comprising:
   acquiring updated patient information after transcranial stimulation; and
   analyzing the updated patent information using reference data.

3. The method of claim 2 further comprising:
electronically determining an updated treatment protocol for the patient.

4. The method of claim 1 further comprising:
determining at least one measured physiological characteristic of the patient, wherein the at least one measured physiological characteristic is selected from the group consisting of heart rate variability, a measure of balance, a measure of at least one of functional cortical brain networks and structural cortical brain networks, a measure of event related potentials, measures of peak performance, and pathology comparisons.

5. The method of claim 1, wherein treatment protocol includes the application of transcranial stimulation consists of at least one of: pulsed transcranial direct current stimulation, non-pulsed transcranial direct current stimulation, transcranial alternating current stimulation and transcranial random noise current stimulation.

6. The method of claim 1 using a network processing environment to determine the treatment protocol.

7. The method of claim 1 further comprising:
receiving a plurality of input data about the patient, the plurality of input data includes at least one of: electronic submission via a patient interface; a diagnosis input code; a DSM diagnosis code; data indicating patient medications; electroencephalogram data; electrocardiogram data; and vestibular balance data.

8. The method of claim 1, wherein said electrodes include at least one anode and at least one cathode such that the at least one anode and the at least one cathode comprise a cluster of an electrode with a first polarity surrounded by at least three electrodes of a second polarity.

9. The method of claim 8, wherein the cluster is a plurality of clusters, and the stimulation is alternated between a first and a second cluster.

10. The method of claim 9, wherein each cluster stimulates a different region of the brain based on the treatment protocols.

11. A transcranial stimulation system comprising:
at least one processing device operative to determine a treatment protocol for a patient based at least on a plurality of good-fit determinations; and
a transcranial current stimulation device including:
a plurality of spaced-apart removable and replaceable at least one of: electrodes and sensors, arranged in a piece of headgear;
an electroencephalography device wired to one or more of said at least one of: electrodes and sensors; and
the transcranial current stimulation device wired to one or more of said electrodes for applying stimulation to the patient based on the treatment protocol.

12. The system of claim 11 further comprising:
at least one input device operative to acquire updated patient information after transcranial stimulation; and
the processing device further operative to analyze the updated patent using reference data.

13. The system of claim 12, the processing device further operative to determine an updated treatment protocol for the patient.

14. The system of claim 12, wherein the processing device is further operative to determine at least one measured physiological characteristic of the patient, wherein the measured physiological characteristic is selected from the group consisting of heart rate variability, a measure of balance, a measure of at least one of functional cortical brain networks and structural cortical brain networks, a measure of event related potentials, measures of peak performance, and pathology comparisons.

15. The system of claim 11, wherein treatment protocol includes the application of transcranial stimulation consists of at least one of: pulsed transcranial direct current stimulation, non-pulsed transcranial direct current stimulation, transcranial alternating current stimulation and transcranial random noise current stimulation.

16. The system of claim 11, wherein the at least one processing device is disposed in a network processing environment.

17. The system of claim 11 further comprising at least one input device to receive a plurality of input data about the patient, the plurality of input data includes at least one of: electronic submission via a patient interface; a diagnosis input code; a DSM diagnosis code; data indicating patient medications; electroencephalogram data; electrocardiogram data; and vestibular balance data.

18. The system of claim 11, wherein said electrodes include at least one anode and at least one cathode, the system further comprising:
a cluster of an electrode with a first polarity surrounded by at least three electrodes of a second polarity.

19. The system of claim 18, wherein the cluster is a plurality of clusters, and the stimulation is alternated between a first and a second cluster.

20. The system of claim 19, wherein each cluster stimulates a different region of the brain based on the treatment protocol.

* * * * *